United States Patent [19]

Suzuki et al.

[11] Patent Number: 5,556,995

[45] Date of Patent: Sep. 17, 1996

[54] PROCESS FOR THE PREPARATION OF POLYHYDRIC PHENOL COMPOUNDS

[75] Inventors: Naoko Suzuki, Amagasaki; Hirotoshi Nakanishi, Osaka; Jun Tomioka, Takarazuka, all of Japan

[73] Assignee: Sumitomo Chemical Co., Ltd., Osaka, Japan

[21] Appl. No.: 378,942

[22] Filed: Jan. 26, 1995

Related U.S. Application Data

[63] Continuation of Ser. No. 93,620, Jul. 20, 1993, abandoned.

[30] Foreign Application Priority Data

Aug. 7, 1992 [JP] Japan ..................... 4-211387

[51] Int. Cl.⁶ .................................. C07D 311/60
[52] U.S. Cl. .................................. 549/406
[58] Field of Search .............................. 549/406

[56] References Cited

U.S. PATENT DOCUMENTS 5,436,107  7/1995  Tomioka et al. .............. 430/192

FOREIGN PATENT DOCUMENTS 505987    9/1992   European Pat. Off. .
55-139375 10/1980  Japan .
61-27980  2/1986   Japan .
4295472   10/1992  Japan .
822659    10/1959  United Kingdom .

*Primary Examiner*—Nicky Chan
*Attorney, Agent, or Firm*—Birch, Stewart, Kolasch & Birch, LLP

[57] ABSTRACT

A process for preparing the polyhydric phenol compounds represented by the formula (I):

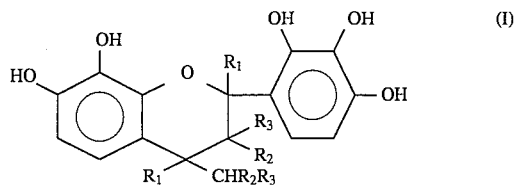

(wherein $R_1$, $R_2$ and $R_3$ represent independently hydrogen atom, alkyl group, etc.) which comprises subjecting the compounds represented by the formula (II):

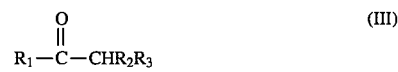

(wherein $R_1$, $R_2$ and $R_3$ are as defined above) to a condensation reaction with pyrogallol in the presence of an organic solvent and an acid catalyst.

13 Claims, No Drawings

PROCESS FOR THE PREPARATION OF POLYHYDRIC PHENOL COMPOUNDS

This application is a continuation of application Ser. No. 08/093,620 filed on Jul. 20, 1993, now abandoned,.

BACKGROUND OF THE INVENTION

1. Field of the Invention

The present invention relates to a process for preparing polyhydric phenol compounds represented by the formula (I):

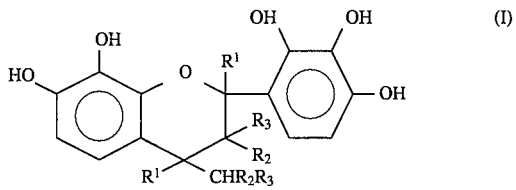

wherein $R_1$, $R_2$ and $R_3$ represent independently hydrogen atom, alkyl, alkenyl, cycloalkyl, aralkyl or aryl group, which are useful as an intermediate of photosensitive agents or sensitizers for photoresists and the like.

2. Related Art

As a method for preparing phenylchroman derivatives which have a structural resemblance to polyhydric phenol compounds, U.K. Patent No. 822,659 discloses a process comprising reacting resorcinol with acetone in a molar ratio of 2:3~2:1 in the presence of an inorganic acid by using water as reaction solvent. This process, however, has a problem that it is unable to produce a polyhydric phenol compound with high purity in a high yield when it is applied to a condensation reaction of a compound represented by the formula (II):

wherein $R_1$, $R_2$ and $R_3$ are as defined above, with pyrogallol.

An object of present invention is to overcome the above problem and provide an industrially advantageous process for producing the polyhydric phenol compounds.

SUMMARY OF THE INVENTION

According to the present invention, there is provided a process for preparing polyhydric phenol compounds represented by the above formula (I), which comprises carrying out a condensation reaction between a compound of the above formula (II) and pyrogallol in the presence of an organic solvent and an acid catalyst.

DESCRIPTION OF THE INVENTION

The alkyl or alkenyl groups and the cycloalkyl groups represented by $R_1$, $R_2$ and $R_3$ in the formula (II) are those having 4 or less carbon atoms and those having 3 to 8 carbon atoms, respectively. Similarly, the aralkyl or aryl groups are those having 12 or less carbon atoms. Preferably $R_1$, $R_2$ and $R_3$ represent hydrogen atom, methyl or ethyl, respectively.

The compounds represented by the formula (II) include aliphatic ketones such as acetone, methyl ethyl ketone and methyl isobutyl ketone, alicyclic ketones such as methyl cyclohexyl ketone, and aromatic ketones such as acetophenone.

The molar ratio of the compound of the formula (II) to pyrogallol is usually 1:1 to 1:10, preferably 1:2 to 1:4.

The acid catalysts usable in the reaction of the present invention include inorganic acids such as hydrogen chloride, sulfuric acid and phosphoric acid, organic acids such as methanesulfonic acid, trichloroacetic acid, trifluoroacetic acid and p-toluenesulfonic acid, and cation exchange resins having a sulfonic group (such as AMBERLIST 15 mfd. by Organo Co., Ltd.). Among these acid catalysts, the organic acids such as mentioned above are preferred, and of these organic acids, p-toluenesulfonic acid is especially preferred. The amount of the acid catalyst used in the reaction of the present invention, although variable depending on the type of the catalyst employed, is usually 0.01 to 1.5 moles, preferably 0.01 to 0.15 moles, per one mole of the compound of the formula (II).

The organic solvents usable in the reaction of the present invention include alcohols such as methanol, ethanol and isopropyl alcohol, acetic acid esters such as methyl acetate, ethyl acetate, n-propyl acetate, isopropyl acetate, n-butyl acetate, isobutyl acetate and n-amyl acetate. Among these organic solvents, the acetic acid esters are preferred, ethyl acetate being especially preferred. The amount of the organic solvent used in the reaction is usually 50 to 500 parts by weight, preferably 110 to 250 parts by weight, per 100 parts by weight of pyrogallol.

The condensation reaction in the present invention is preferably carried out by supplying continuously or intermittently (preferably continuously) a compound of the formula (II) into a mixture of pyrogallol, an acid catalyst and an organic solvent. This reaction is usually conducted at a temperature within the range of 20° to 100° C., preferably 35° to 65° C. The reaction time is usually 1 to 72 hours, preferably 3 to 30 hours. It is desirable to neutralize the reaction mixture with an alkali, preferably immediately after the end of the condensation reaction.

The alkalis usable for such neutralization include ammonia, ammonium salts such as, ammonium carbonate and ammonium acetate, and alkali metal salts such as potassium phosphate and sodium phosphate. These alkalis are usually used in the form of an aqueous solution. The amount of the alkali used for said purpose is usually 1 to 10 moles, preferably 1.2 to 7 moles, per one mole of the acid catalyst. The neutralization temperature is usually 5° to 70° C., preferably 20° to 65° C.

In case an acetic acid ester is used as the organic solvent, the neutralized reaction mixture is usually washed with water in the form as it is. However, in case an alcohol is used as the organic solvent, the reaction mixture needs to be added with an extraction solvent such as ethyl acetate or toluene and then washed with water. After washing with water, the formed organic layer may be immediately reacted with a pertinent compound such as quinonediazidosulfonic acid halide for use as a sensitizer, but usually, before worked into a sensitizer, said organic layer is subjected to a treatment, such as distillation, for removing the organic solvent and the extraction solvent. This solvent removing treatment is usually conducted in such a way that the solvent content after the treatment will become less than 20% by weight, preferably less than 5% by weight. The resulting material may be reacted with quinonediazidosulfonic acid halide or other pertinent compound to form a sensitizer, but it is preferable to isolate the polyhydric phenol compound through recrystallization by using water, etc.

The amount of water used for recrystallization is usually 15% to 80% by weight, preferably 20% to 70% by weight, in the mixture of the solvent-removed material and water. The amount of pyrogallol at the time of recrystallization is preferably about 6% to 40% by weight, more preferably about 8% to 35% by weight. The recrystallization temperature is usually 5° to 70° C., preferably 20° to 60° C. If necessary, seed crystals may be added at the time of recrystallization. The crystals which separate out in the process of recrystallization are isolated by using usual means such as filtration, washing with water and drying.

PREFERRED EMBODIMENTS

The present invention will be described more particularly below by showing the examples thereof, which examples however are merely intended to be illustrative and not to be construed as limiting the scope of the invention in any way. In the following Examples, the measurements (absolute calibration method) by HPLC (LC-6A mfd. by Shimadzu Corp.) were made under the following conditions:

Column: Sumipax ODS A-212

Mobile phase A: 0.5% formic acid/deionized distilled water

Mobile phase B: 0.5% formic acid/acetonitrile

Flow rate: 1.5 ml/min

Detector: UV 280 nm

Regarding the mobile phases, the initial phase proportion were set to be A/B=90/10, and the mobile phase B proportion was increased at a rate of 3% per minute so that the final proportion would become A/B=0/100.

EXAMPLE 1

Into a mixture of 85.6 g (0.68 mol) of pyrogallol, 2.6 g (0.014 mol) of p-toluenesulfonic acid and 171.2 g of ethyl acetate, 13.0 g (0.22 mol) of acetone was added dropwise with stirring at 38°–42° C. over a period of 30 minutes. After completion of the dropwise addition, the mixture was reacted at the same temperature for 20 hours.

After the end of the reaction, the reaction mixture was neutralized with 3.4 g of 28% ammonia water at 38°–42° C. Thereafter, 91 g of water was added and the mixture was heated to 58°–62° C. After washing at the same temperature, the liquid was separated to obtain an organic layer. 91 g of water was added to the obtained organic layer, followed by washing and separation of the liquid. This operation was repeated once more, and resultantly obtained 225 g of organic layer was concentrated under the conditions of 70°–85° C. and 150 Torr to obtain 80 g of an oily substance. 8 g of water was added to this substance and the substance was recrystallized with stirring under the condition of 23°–25° C. for 20 hours. The resulting crystals were filtered, and the obtained cake was compressed well to remove the mother liquor and then washed with 30 g of water. This washing operation was repeated two more times and the obtained cake was dried under the conditions of 80° C., 20–40 Torr and 24 hours to give 13.4 g of a compound represented by the following formula (yield based on acetone=36%; purity as determined by HPLC=97% ):

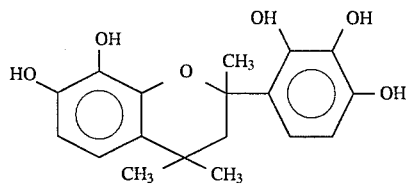

$^1$HNMR spectrum (solvent: acetone d6, TMS) chemical shifts: 0.80 ppm (s, 3H), 1.23 ppm (s, 3H), 1.69 ppm (s, 3H), 1.90 ppm (d, 1H, J=approx. 14 Hz), 3.01 ppm (d, 1H, J=approx. 14 Hz), 6.23 ppm (d, 1H, J=8.6 Hz), 6.42 ppm (d, 1H, J=8.6 Hz), 6.50 ppm (d, 1H, J=8.6 Hz), 6.57 ppm (d, 1H, J=8.6 Hz), about 7.5 ppm (s, 5H).

Mass spectrum m/e: 332 (M+)

Melting point: 183°–184° C.

EXAMPLE 2

Into a mixture of 945.8 g (7.50 mol) of pyrogallol, 29.3 g (0.15 mol) of p-toluenesulfonic acid and 1,892 g of ethyl acetate, 145.2 g (2.50 mol) of acetone was added dropwise with stirring at 38°–42° C. over a period of one hour, after which the mixture was reacted at the same temperature for 20 hours.

The reaction mixture was neutralized with 62.5 g of 28% ammonia water at 38°–42° C. Thereafter, 1,500 g of water was added and the mixture was heated to 58°–62° C. After washing at the same temperature, the liquid was separated to obtain an organic layer. 1,500 g of water was added to the organic layer, followed by washing and separation of the liquid. This operation was repeated twice to obtain 2,376 g of the organic layer, followed by concentration at 60°–80° C. under reduced pressure to give an oily substance. Water was added to the oily substance, followed by concentration under reduced pressure to give 700 g of an oily substance. 462 g of water was added to the substance and it was recrystallized with stirring at 25°–27° C. for 18 hours. The resulting crystals were filtered and the obtained cake was compressed well to remove the mother liquor, followed by washing with 300 g of water. This washing operation was repeated two more times and the resulting cake was dried under the conditions of 70° C., 20–40 Torr and 24 hours to give a polyhydric phenol compound which is same to the compound as obtained in Example 1 (yield based on acetone: 40.8%; purity as determined HPLC: 94.5%).

Comparative Example 1

Into a mixture of 98.4 g (0.78 mol) of pyrogallol, 13.9 g (0.07 mol) of p-toluenesulfonic acid and 49.2 g of water, 34.8 g (0.60 mol) of acetone was added dropwise, with stirring at 38°–42° C. over a period of 30 minutes. After the end of the dropwise addition, the mixture was reacted at the same temperature for 70 hours. Thereafter, the reaction mixture was neutralized with 9 g of 28% ammonia water at 38°–42° C. Then 200 g of ethyl acetate and 115 g of water were added to the mixture, followed by washing of the mixture and separation of the liquid to obtain an organic layer. 115 g of water was added to the obtained organic layer, followed by washing thereof and separation of the liquid. This operation was repeated once more and the resulting organic layer was concentrated to obtain 101 g of an oily substance. 12 g of ethyl acetate and 166 g of toluene were added to the oily substance. The resulting mixture was recrystallized with stirring. The resulting crystals were filtered and the cake thus obtained was compressed well to remove the mother liquor. This cake was dried under the conditions of 80° C., 20–40 Torr and 20 hours to give a polyhydric phenol compound which is same to the compound as obtained in Example 1 (yield based on acetone: 15%; purity as determined by HPLC: 93%).

EXAMPLE 3

257.3 g of pyrogallol and 92.3 g of 36% hydrochloric acid were added to 280 g of methanol, and the mixture was heated to 45°–50° C. with stirring to form a homogeneous solution. 34.8 g of acetone was added dropwise to the solution over a period of 30 minutes, after which the mixture was further stirred at the same temperature for 8 hours. After completion of the reaction, 4 litres of water and 1.1 litre of ethyl acetate were added to the resulting reaction solution and then the liquid was separated to obtain an organic layer. To the organic layer, 3 litres of water, 200 ml of ethyl acetate and 150 ml of toluene were added, followed by washing with water. Then the liquid was separated and the organic layer thus obtained was washed with 3 litres of water. After 2 more times of washing with water, the resulting organic layer was concentrated to obtain 103 g of an oily substance. The oily substance was recrystallized by adding 13 g of ethyl acetate and 170 g of toluene and dried at 70° C. to give 2.6 g of a polyhydric phenol compound.

Referential Example 1

6.64 g of the compound obtained in Example 1, 24.18 g of naphthoquinone-(1,2)-diazido-(2)-5-sulfonic acid chloride (molar ratio of said compound to the above chloride; 1:4.5) and 150 g of dioxane were charged into a 300 ml three-necked flask and completely dissolved by stirring. Then 10.0 g of triethylamine was added dropwise into the mixture with stirring over a period of 30 minutes while controlling the reaction temperature at 20°–25° C. by immersing the flask in a water bath. Thereafter, the mixture was further stirred at the same temperature for 20 hours. On completion of the reaction, the reaction mixture was poured into deionized water, followed by filtration and drying to obtain a sensitizing agent (esterifcation: 90%).

What is claimed is:

1. A process for preparing a polyhydric phenol compound represented by the formula (1):

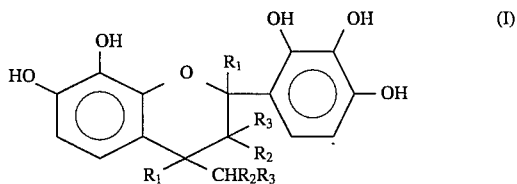

wherein $R_1$, $R_2$ and $R_3$ independently represent hydrogen atom, alkyl, alkenyl, cycloalkyl, aralkyl or aryl group, which comprises carrying out a condensation reaction between a compound represented by the formula (II):

wherein $R_1$, $R_2$ and $R_3$ are as defined above, and pyrogallol in the presence of ethyl acetate and an organic acid catalyst.

2. The process according to claim 1, wherein said organic acid is p-toluenesulfonic acid.

3. The process according to claim 1, further comprising neutralizing the reaction mixture after the condensation reaction with an alkali.

4. The process according to claim 1, further comprising isolating the polyhydric phenol compound by recrystallization using water.

5. The process according to claim 1, wherein said compound represented by formula (II) is an aliphatic ketone.

6. The process according to claim 5, wherein said aliphatic ketone is selected from the group consisting of acetone, methyl ethyl ketone and methyl isobutyl ketone.

7. The process according to claim 1, wherein said compound represented by formula (II) is selected from the group consisting of methyl cyclohexyl ketone and acetophenone.

8. The process according to claim 1, wherein the molar ratio of said compound represented by formula (II) to pyrogallol is from 1:1 to 1:10 in said condensation reaction.

9. The process according to claim 1, wherein the molar ratio of said compound represented by formula (II) to pyrogallol is from 1:2 to 1:4 in said condensation reaction.

10. The process according to claim 1, wherein said organic acid catalyst is selected from the group consisting of methanesulfonic acid, trichloroacetic acid, trifluoroacetic acid and p-toluenesulfonic acid.

11. The process according to claim 1, wherein said organic acid catalyst is used in said condensation reaction in an amount of 0.01 to 1.5 moles per one mole of said compound represented by formula (II).

12. The process according to claim 1, wherein said organic solvent is used in said condensation reaction in an amount of 50 to 500 parts by weight per 100 parts by weight of pyrogallol.

13. The process according to claim 1, wherein said ethyl acetate is used in said condensation reaction in an amount of 110 to 250 parts by weight per 100 parts by weight of pyrogallol.

* * * * *